United States Patent [19]
Emini et al.

[11] Patent Number: 4,596,674
[45] Date of Patent: Jun. 24, 1986

[54] IMMUNOGENIC HAV PEPTIDES

[75] Inventors: Emilio A. Emini, Paoli, Pa.; Joshua S. Boger, Westfield, N.J.; Joseph V. Hughes, Harleysville, Pa.

[73] Assignee: Merck & Co., Inc., Rahway, N.J.

[21] Appl. No.: 649,388

[22] Filed: Sep. 11, 1984

[51] Int. Cl.[4] .......................... C07K 7/08; C07K 7/06; C07K 7/10
[52] U.S. Cl. .................................. 530/326; 530/329; 530/328; 530/327; 530/807
[58] Field of Search ................................ 260/112.5 R

[56] References Cited

PUBLICATIONS

Beale, Nature 298: 14–15, Jul. 1, 1982.
Arnon et al., Journal of Immunological Methods 61: 261–273, 83.
Shinnick et al., Ann. Rev. Microbiol 37: 425–446, 1983.
Emini et al., Nature 304: 699–703, 8/25/83.

*Primary Examiner*—Delbert R. Phillips
*Attorney, Agent, or Firm*—Donald J. Perrella; Hesna J. Pfeiffer

[57] ABSTRACT

Synthetic peptides, containing amino acid residues 15 to 21, 75–80 and 101–107 of the hepatitis A virus (HAV) VP1 structural protein sequence, was prepared and chemically conjugated to a protein carrier molecule. The peptide-carrier conjugate, when inoculated into test animals, gives rise to a specific anti-peptide IgG antibody response. These anti-peptide antibodies bind directly to intact hepatitis A virions, bind to purified and denatured VP1, compete with polyspecific antibody derived from human HAV immune sera, and are capable of neutralizing the infectivity of the virus. The peptide is useful as a synthetic subunit immunogen that stimulates an immune response against HAV.

9 Claims, No Drawings

IMMUNOGENIC HAV PEPTIDES

BACKGROUND OF THE INVENTION

Hepatitis A is a liver disease which, although not commonly fatal, can induce long periods of debilitating illness. The disease is commonly spread by direct contact with an infected individual or by HAV contaminated drinking water and/or food.

No easily obtainable immunogen which will induce neutralizing antibody against the virus is available. The virus itself is difficult to cultivate and production of sufficient quantities for use as a live or killed vaccine is not presently feasible.

SUMMARY OF THE INVENTION

A peptide, containing amino acid residues 13 to 24 of the VP1 structural protein of HAV, was synthesized and chemically conjugated to a carrier protein molecule. The peptide-carrier conjugate elicits, in animals, antibodies which bind to hepatitis A virions and which neutralize the infectivity of the virus. The peptide is useful as a synthetic immunogen which specifically induces the production of HAV-neutralizing antibodies.

DETAILED DESCRIPTION OF THE INVENTION

I. SELECTION OF PEPTIDE SEQUENCES

Immunogenic peptides from three areas of the hepatitis A VPl protein sequence have been identified. These peptides comprise a core one of the following sequences wherein the number indicates the position of the amino acids in the HAV VPl protein sequence:

15 ... 21
Glu—Gln—Asn—Val—Pro—Asp—Pro (A)

75 ... 80
Glu—Ser—Arg—His—Thr—Ser (B)

101 ... 107
Asn—Ser—Asn—Asn—Lys—Glu—Tyr (C)

and may be extended on either side by amino acids contained in the natural sequence up to and including the sequences listed:

9 10 ... 15 ... 20 ... 24
Ser—Thr—Thr—Val—Ser—Thr—<u>Glu—Gln—Asn—Val—Pro—Asp—Pro</u>—Gln—Val—Gly (A)

69 70 ... 75 ... 80 ... 84
Pro—Glu—Leu—Lys—Pro—Gly—<u>Glu—Ser—Arg—His—Thr—Ser</u>—Asp—His—Met—Ser (B)

96 ... 100 ... 105 ... 110 112
Cys—Thr—Phe—Thr—Phe—<u>Asn—Ser—Asn—Asn—Lys—Glu—Tyr</u>—Thr—Phe—Pro—Ile—Thr (C)

In addition, to each sequence may be added one or more linker amino acids, such as Lys (free or side-chain acylated with a photoreactive group), Tyr, Cys, Glu, or Asp, at either or both N or C terminus to facilitate the conjugation to a carrier. In addition the sequence may include one or more spacer amino acids of, for example Gly, Ala, or Nle, included between the natural sequence and the linker amino acids, or at the N or C terminus itself. The peptide terminae may be free amino, amino acylated with p-benzoylbenzoyl (or other photoreactive group), or N-acetyl (or other alkyl carboxyl) and free carboxy or amide.

Preferred sequences are:

(1) Ac-Tyr-Nle-Ser-Thr-Glu-Gln-Asn-Val-Pro-Asp-Pro-Gln-Val-Gly-Cys-$NH_2$ (2) Ac-Lys-Nle-Val-Ser-Thr-Glu-Gln-Asn-Val-Pro-Asp-Pro-Gln-Val-Gly-Nle-$NH_2$ (3) Ac-Lys(BB)-Nle-Val-Ser-Thr-Glu-Gln-Asn-Val-Pro-Asp-Pro-Gln-Val-Gly-Nle-$NH_2$ (4) Ac-Tyr-Pro-Glu-Leu-Lys-Pro-Gly-Glu-Ser-Arg-His-Thr-Ser-Asp-His-Nle-Ser-Cys-$NH_2$ (5) Ac-Cys-Thr-Phe-Thr-Phe-Asn-Ser-Asn-Asn-Lys-Glu-Tyr-Thr-Phe-Pro-Nle-$NH_2$ (6) Ac-Thr-Phe-Thr-Phe-Asn-Ser-Asn-Asn-Lys-Glu-Tyr-Thr-Phe-Pro-Nle-Cys-$NH_2$

Where Cys may be either free thiol (for linking to carrier) or as an Acm derivative. BB = p-benzoylbenzoyl.

II. PEPTIDE SYNTHESIS

The peptides described here are made by solid phase sequential synthesis, beginning from the C-terminus, according to procedures described by Barany & Merrifield (in "The Peptides", Vol. 2, Ed., E. Gross & J. Meienhofer, pp. 1–284, Academic Press, New York, N.Y., 1980), using a Beckman 990B peptide synthesizer to carry out the operations according to the attached. programs. The starting polymer beads are a p-methylbenzhydrylamine-functionalized polystyrene-divinylbenzene (PS-DVB, 1% cross-linked, see Stewart et al., "Peptides 1976", Ed., A. Loffet, pp. 285–290, Editions de l'Universite de Bruxelles, Belgium, 1976), when the C-terminus is to be an amide, or a chloromethyl-functionalized PS-DVB when the C-terminus is to be a free acid. The C-terminal amino acid of the desired sequence is attached, as its N-protected and side chain-protected (when necessary) derivative, to the resin either as an amide according to the same procedures used for chain elongation, in the case of a p-methylbenzhydrylamine resin, or by an ester linkage, as described in Barany & Merrifield, supra, for the chloromethyl substituted resin. Initial amino acid loading is 0.1–1.1 mmoles/g of starting resin. In the case of the benzhydrylamine resin, remaining amine sites are blocked using acetic anhydride/pyridine before proceeding with chain elongation.

After the amino-protecting group is removed, using 25–40% TFA in $CH_2Cl_2$, containing 1% EDT, or 4N HCl in dioxane, the protected derivative of the next amino acid is added, along with a coupling reagent, if necessary such as DCC, along with additives such as HBT. The amino acid reactant may be employed in the form of a carboxyl-activated amino acid such as an nitrophenyl ester, an amino acid azide, and the like. A coupling reaction may be repeated in order to obtain complete reaction. Deprotection and addition of successive amino acids is performed until the desired sequence is formed. Coupling reactions using DCC-activated Gln or Asn use two equivalents of HBT to suppress side-chain dehydration. Alpha-amino Boc-deprotection of Gln on the growing chain is done preferably using HCl in dioxane, and the subsequent protected amino acid is coupled using a reverse-addition protocol, in which the coupling agent, in the case of DCC, is added to the resin before the amino acid component. This suppresses pyroglutamic acid formation, a side reaction.

The selection of protecting groups is, in part, dictated by coupling conditions, in part by the amino acid and peptide components involved in the reaction. Amino-protecting groups ordinarily employed include those well known in the art, for example, urethane protecting substituents such as benzyloxycarbonyl ("CBZ"), tert-butyloxycarbonyl ("Boc"), and the like. Boc is preferred for protecting the alpha-amino group in the amino acids undergoing reaction at the carboxyl end of said amino acid. The Boc protecting group is easily removed using TFA, as mentioned above, or other acids such as HCl (3M in dioxane).

The epsilon-amino group of Lys can be protected by the CBZ group, or preferably by 2-Cl-CBZ group. The OH of Tyr is protected preferably using the 2,6-$Cl_2$-Bzl group, although the Bzl group may be used where the Tyr residue is toward the N-terminal side of the desired sequence. The OH group of THr and Ser can be protected by the Bzl group. Arg is protected with the nitro group. Glu and Asp are protected as their benzyl esters. His is protected as its DNP derivative. Cys is protected as the Acm derivative. These groups are relatively stable to the action of TFA used to remove the Boc group at each step. After the peptide sequence is formed, these protecting groups, except for Acm and DNP, can be removed by the action of HF or by hydrogenation. The DNP group is removed preferably by the action of thiophenol (10% in DMF) as a final resin program, although this reaction may be run in solution with the free peptide. The Acm group can be removed from the free peptide by Hg to give the free Cys or by $I_2$ to give a disulfide.

After the peptide has been formed on the resin, it may be removed by several well-known methods appropriate to the particular resin, preferably using liquid HF in a low-high procedure as described by Tam et al., *Int. J. Peptide Protein Res.*, 21: 57–65, 1983, and references therein. Purification of the peptides uses Sephadex sizing chromatography (G-15, G-25, and G-50, depending on the peptide size) in either 50% or 2N acetic acid, and reverse phase HPLC on C-18 reverse phase columns, when necessary, using gradient elutions from dilute TFA (0.1%) or trimethylamine phosphate (pH3.2) or acetonitrile.

Peptide products are characterized primarily by amino acid analyses performed on a Beckman 121MB or Beckman 6300 analyzer after 70 hours hydrolyses in 6N HCl. The peptide product is checked by HPLC and is found generally to be 50–70% homogeneous.

III. CONJUGATION PROCEDURES

In order to enhance peptide immunogenicity, the peptides described here are usually covalently linked ("conjugated") to a larger molecule which serves as a carrier. Carriers can include proteins such as heterologous serum albumins, keyhole limpet hemocyanin, diphtheria toxoid, etc. or synthetic polymers such as poly(D-Glu,D-Lys). Attachment of the peptide to the carrier can be by one of several methods, including linking through a peptide Lys using glutaraldehyde (Reichlin, *Methods Enzymol.* 70: 159–165, 1980) or DCC procedures (for example, Atassi et al., *Biochem. Biophys. Acta* 670: 300–302, 1981), through a peptide Asp or Glu using DCC (Bauminger et al., *Methods Enzymol.* 70: 151–159, 1980), through a peptide Tyr using bis-diazotized benzidine (Walter et al., *Proc. Nat. Acad. Sci. USA* 77: 5197–5200, 1980), through photochemical attachment sites (Parker et al., *Cold Spring Harbor Symposium-Modern Approaches to Vaccines*, Ed. Chanock & Lerner, Cold Spring Harbor Press, New York, 1983, in press), or through a peptide Cys (Liu et al., *Biochem.* 18: 690–697, 1979). Peptide carrier conjugates are separated from excess free peptide by dialysis or gel filtration. The level of loading of the peptide on the carrier can be determined either using a radioactive tracer to establish the loading level in a particular procedure, or by quantitative amino acid analysis of the conjugate, in comparison with the unloaded carrier. It is convenient, when using the latter technique, to incorporate a unique non-natural amino acid into the peptide, at the N-terminal or C-terminal side, such as Nle, which can then serve as a quantitative marker for peptide incorporation, as measured by amino acid analysis of the conjugate. This Nle can also function as a spacer between the antigenic site and any amino acid incorporated to facilitate attachment, such as Cys, Lys, or Tyr, as described above.

The peptides of the present invention, either free or conjugated, may be administered in a physiologically acceptable carrier to a susceptible mammalian species to protect against HAV disease.

EXAMPLE 1

Synthesis of
N-Acetyl-L-Tyrosyl-L-Norleucyl-L-Seryl-L-Threonyl-L-Glutamyl-L-Glutaminyl-L-Asparaginyl-L-Valyl-L-Prolyl-L-Aspartyl-L-Prolyl-L-Glutaminyl-L-Valyl-Glycyl-L-(S-Acetamidomethyl)-Cysteinyl Amide The title sequence was synthesized on a Beckman 990B peptide synthesizer or p-methylbenzhydrylamine resin according to general solid phase synthetic procedures as described by Barany & Merrifield, "The Peptides", Vol. 2, Ed., E. Gross & J. Meienhofer, pp. 1–284, Academic Press, New York, N.Y., 1980. Specifically, the initial Boc-(Acm)-Cys was loaded onto the p-methyl benzhydrylamine resin (nominal amine content of 0.414 mmol N per g), using Program 2 (run twice), followed by capping of any unreacted amine sites using acetic anhydride/pyridine (10 equivalents each) and Program 4. This starting resin was analyzed by elemental analysis and found to contain approximately 0.3 mmol/g of Boc-(Acm)-Cys, as judged by the sulfur analysis. Synthesis was continued on a 1 mmol scale (3.33 g Boc-(Acm)-Cys-NH-Resin), adding successive protected amino acids to the growing N-terminus, according to Programs 1 (for Boc-removal and coupling), 2 (for recoupling), 5 & 6 (for coupling and recoupling following Gln, and 3 & 4 (for terminal acetylation, using 10 equivalents of acetic anhydride/pyridine). Boc-protection was used throughout for alpha-amino temporary protection. Asp and Glu side chains were protected as the o-benzyl esters. Ser and Thr side chains were protected as the o-benzyl ethers. Tyr side chain was protected as the 2,6-$Cl_2$-benzyl ether. All couplings and recouplings used a 2.5 equivalent excess of amino acid over peptide chain. Two recouplings were done at every step. Couplings and recouplings used DCC with HBT added to each amino acid solution (each 2.5 equivalents versus the nominal starting resin). The completed resin, dried in vacuo, weighed 4.85 g.

A 1.85 g portion of this peptide resin was treated in a "low-high" HF deprotection/removal, according to the procedures described by Tam et al., *Int. J. Peptide Protein Res.*, 21: 57–65, 1983. Briefly, the resin was placed in the vessel of a standard HF-Reaction Apparatus (Peninsula Laboratories). To the resin was added 1.5 ml m-cresol and 6.5 ml dimethyl sulfide. This was cooled to −78° C. and 2.5 ml HF was condensed into the reaction. This was stirred at 0° C. for 2 hours, and the HF was removed under water aspiration for 30 minutes at 0° C., followed by aspiration for 45 minutes at room temperature for dimethyl sulfide removal. After trituration with ether and drying, the resin was placed back in the HF apparatus with 1.5 ml m-cresol, cooled to −78° C., and 20 ml HF was condensed in. This was stirred at 0° C. for 1 hour, after which the HF was removed by water aspiration, at 0° C. The resin and product were washed and decanted with petroleum ether, triturated with ethyl acetate, and filtered. The solid was then suspended in 50 ml of 50% acetic acid, solubilizing the peptide product, and placed directly onto a G-15 Sephadex chromatography column prepared and eluted with 50% acetic acid. The column showed two large peaks, and the material eluting just after the void volume was combined and stripped to a film.

This crude peptide material was applied to a G-50 Sephadex chromatography column, packed and eluted with 50% acetic acid. Fractions were examined by reverse phase HPLC (C-18 column, 0.1% TFA/acetonitril gradient elution), and fractions containing the major 210 nm absorbing material were combined and evaporated. This material was freeze-dried, giving 244 mg of the title peptide, judged to be a single major component by HPLC and not requiring additional purification. Amino acid analysis gave: Asx (Asp+Asn) 2.07, Thr 1.00, Ser. 0.94, Glx (Glu+Gln) 2.99, Pro 2.42 (interference with Cys degradation products makes this number too large), Gly 1.06, Val 2.11, Tyr 0.90, and Nle 0.93. The product is 82% peptide (the rest being salts and water) based on molecular weight of 1729.9.

EXAMPLE 2

Synthesis of bovine-serum albumin conjugate of AC-Tyr-Nle-Ser-Thr-Glu-Gln-Asn-Val-Pro-Gln-Val-Gly-Cys-NH$_2$ The title peptide sequence was conjugated to bovine serum albumin (BSA) derivatized with m-maleimidobenzoyl-N-hydroxysuccinimide ester (MBS) according to the procedures described by Liu et al., Biochem. 18: 690–697, 1979. The initial MBS derivative of BSA can be prepared exactly as described by Liu et al., for ovalbumin, using MBS and BSA in pH 7.0 phosphate buffer, and purified by Sephadex column chromatography. For large batches of the BSA-MBS adduct ("MB-BSA"), dialysis was used more conveniently for the removal of excess reactants. The number of maleimide groups attached to each BSA was determined, by the method outlined by Liu, et al., to be 2.0–2.5, based upon protein content determined by amino acid analysis.

For conjugation to MS-BSA, the Cys-protected peptide described in Example 1 was converted to its free thiol Cys analog. This was done in two steps. First, the Acm group was removed and the thiol oxidized to the symmetrical disulfide by the action of I$_2$, and this symmetrical disulfide was reduced to the free Cys-peptide with dithiothreitol (DTT). Briefly, 50 mg of the Cys-protected peptide described in Example 1 was dissolved in 1.8 ml of 99% acetic acid (1% water) plus 1 drop of DMF, containing 0.29 mmol I$_2$ in solution. This solution was stirred for 2 hours at room temperature, and the reaction was quenched by the addition of 200 mgs moist Zn dust. The suspension was filtered and the solid washed with 50% acetic acid. The filtrate was applied directly to a G-50 Sephadex chromatography column, packed and eluted with 50% acetic acid. Fractions of the first large peak were combined and freeze-dried, giving 24 mg of symmetrical disulfide-linked peptide.

A 5 mg portion of this disulfide peptide dimer was reduced by dissolving in 1 ml pH 6.0 (phosphate) buffer under argon, adding 1.5 mg DTT, and stirring for 30 minutes. This solution was applied directly to a short (7 ml total volume) Sephadex G-25 chromatography column, packed and eluted with degassed pH 6.0 buffer at 0° C. The peak eluting with the void volume was collected, avoiding contamination with the slower-running DTT peak, and 100 mg of the MB-BSA was added immediately. This reaction was kept at 0° C. overnight and quenched by the addition of 20 μl of 2-mercaptoethanol. The quenched reaction was applied to a Sephadex G-100 chromatography column, packed and eluted with pH 6.0 phosphate buffer. The double peak, representing approximately 1:1 BSA-conjugate monomer and higher polymers of BSA-conjugate, was combined and dialyzed against several changes of water for 4 days at 5° C. This material was freeze-dried, giving 119 mg of peptide-BSA conjugate. Amino acid analysis gave a peptide content of approximately 85%, with a loading of 0.42 peptide per BSA unit, based on the Nle amino acid analysis.

| STEP | REAGENT/SOLVENT | VOL. ML | MIXING TIME (MIN.) |
|---|---|---|---|
| COUPLING: PROGRAM 1 | | | |
| 1 | CH$_2$Cl$_2$ | 4 × 20 | 2 |
| 2 | 40% TFA in CH$_2$Cl$_2$ | 2 × 20 | 2 |
| 3 | 40% TFA in CH$_2$Cl$_2$ | 1 × 20 | 25 |
| 4 | CH$_2$Cl$_2$ | 3 × 20 | 2 |
| 5 | 10% TEA in isopropanol | 2 × 20 | 5 |
| 6 | CH$_2$Cl$_2$ | 3 × 20 | 2 |
| 7 | 10% TEA in CH$_2$Cl$_2$ | 2 × 20 | 5 |
| 8 | CH$_2$Cl$_2$ | 4 × 20 | 2 |
| 9 | Boc-amino acid & HBT (2.5 equiv. each) in 2:1 DMF/CH$_2$Cl$_2$, mix and hold (no drain) | 1 × 15 | 5 |
| 10 | 0.5 M DCC in CH$_2$Cl$_2$ | 1 × 5 | 30 |
| 11 | DMF | 1 × 20 | 2 |
| 12 | Methanol | 2 × 20 | 2 |
| 13 | CH$_2$Cl$_2$ | 2 × 20 | 2 |
| 14 | Methanol | 1 × 20 | 2 |
| 15 | CH$_2$Cl$_2$ | 1 × 20 | 2 |
| RECOUPLING: PROGRAM 2 | | | |
| 1 | CH$_2$Cl$_2$ | 3 × 20 | 2 |
| 2 | 10% TEA in CH$_2$Cl$_2$ | 2 × 20 | 5 |
| 3 | CH$_2$Cl$_2$ | 3 × 20 | 2 |
| 4 | Boc-amino acid & HBT (2.5 equiv. each) in 2:1 DMF/CH$_2$Cl$_2$, mix and hold (no drain) | 1 × 15 | 5 |
| 5 | 0.5 M DCC in CH$_2$Cl$_2$ | 1 × 5 | 30 |
| 6 | DMF | 1 × 20 | 2 |
| 7 | Methanol | 2 × 20 | 2 |
| 8 | CH$_2$Cl$_2$ | 2 × 20 | 2 |
| 9 | Methanol | 1 × 20 | 2 |
| 10 | CH$_2$Cl$_2$ | 1 × 20 | 2 |

| STEP | REAGENT/SOLVENT | VOL. ML | MIXING TIME (MIN.) |
|---|---|---|---|
| COUPLING WITHOUT DCC: PROGRAM 3 | | | |
| 1 | $CH_2Cl_2$ | 4 × 20 | 2 |
| 2 | 40% TFA in $CH_2Cl_2$ | 2 × 20 | 2 |
| 3 | 40% TFA in $CH_2Cl_2$ | 1 × 20 | 25 |
| 4 | $CH_2Cl_2$ | 3 × 20 | 2 |
| 5 | 10% TEA in isopropanol | 2 × 20 | 5 |
| 6 | $CH_2Cl_2$ | 3 × 20 | 2 |
| 7 | 10% TEA in $CH_2Cl_2$ | 2 × 20 | 5 |
| 8 | $CH_2Cl_2$ | 4 × 20 | 2 |
| 9 | Boc-amino acid active ester or acetic anhydride/pyridine (2.5 equiv. each) in 2:1 DMF/$CH_2Cl_2$ | 1 × 20 | 60 |
| 10 | DMF | 1 × 20 | 2 |
| 11 | Methanol | 2 × 20 | 2 |
| 12 | $CH_2Cl_2$ | 2 × 20 | 2 |
| 13 | Methanol | 1 × 20 | 2 |
| 14 | $CH_2Cl_2$ | 1 × 20 | 2 |

Coupling may be run for up to 18 hours in some cases.

| STEP | REAGENT/SOLVENT | VOL. ML | MIXING TIME (MIN.) |
|---|---|---|---|
| RECOUPLING WITHOUT DCC: PROGRAM 4 | | | |
| 1 | $CH_2Cl_2$ | 3 × 20 | 2 |
| 2 | 10% TEA in $CH_2Cl_2$ | 2 × 20 | 5 |
| 3 | $CH_2Cl_2$ | 3 × 20 | 2 |
| 4 | Boc-amino acid active ester or acetic anhydride/pyridine (2.5 equiv. each) in 2:1 DMF/$CH_2Cl_2$ | 1 × 20 | 60 |
| 5 | DMF | 1 × 20 | 2 |
| 6 | Methanol | 2 × 20 | 2 |
| 7 | $CH_2Cl_2$ | 2 × 20 | 2 |
| 8 | Methanol | 1 × 20 | 2 |
| 9 | $CH_2Cl_2$ | 1 × 20 | 2 |

Coupling may be run for up to 18 hours in some cases.

| STEP | REAGENT/SOLVENT | VOL. ML | MIXING TIME (MIN.) |
|---|---|---|---|
| COUPLING, INVERSE ADDITION: PROGRAM 5 | | | |
| 1 | $CH_2Cl_2$ | 4 × 20 | 2 |
| 2 | 4N HCl in dioxane | 2 × 20 | 2 |
| 3 | 4N HCl in dioxane | 1 × 20 | 25 |
| 4 | $CH_2Cl_2$ | 3 × 20 | 2 |
| 5 | 10% TEA in isopropanol | 2 × 20 | 5 |
| 6 | $CH_2Cl_2$ | 3 × 20 | 2 |
| 7 | 10% TEA in $CH_2Cl_2$ | 2 × 20 | 5 |
| 8 | $CH_2Cl_2$ | 4 × 20 | 2 |
| 9 | 0.5 M DCC in $CH_2Cl_2$, mix and hold (no drain) | 1 × 5 | 5 |
| 10 | Boc-amino acid & HBT (2.5 equiv. each) in 2:1 DMF/$CH_2Cl_2$ | 1 × 15 | 30 |
| 11 | DMF | 1 × 20 | 2 |
| 12 | Methanol | 2 × 20 | 2 |
| 13 | $CH_2Cl_2$ | 2 × 20 | 2 |
| 14 | Methanol | 1 × 20 | 2 |
| 15 | $CH_2Cl_2$ | 1 × 20 | 2 |

| STEP | REAGENT/SOLVENT | VOL. ML | MIXING TIME (MIN.) |
|---|---|---|---|
| RECOUPLING WITH INVERSE ADDITION: PROGRAM 6 | | | |
| 1 | $CH_2Cl_2$ | 3 × 20 | 2 |
| 2 | 10% TEA in $CH_2Cl_2$ | 2 × 20 | 5 |
| 3 | $CH_2Cl_2$ | 3 × 20 | 2 |
| 4 | 0.5 M DCC in $CH_2Cl_2$, mix and hold (no drain) | 1 × 5 | 5 |
| 5 | Boc-amino acid & HBT (2.5 equiv. each) in 2:1 DMF/$CH_2Cl_2$ | 1 × 15 | 30 |
| 6 | DMF | 1 × 20 | 2 |
| 7 | Methanol | 2 × 20 | 2 |
| 8 | $CH_2Cl_2$ | 2 × 20 | 2 |
| 9 | Methanol | 1 × 20 | 2 |
| 10 | $CH_2Cl_2$ | 1 × 20 | 2 |

| STEP | REAGENT/SOLVENT | VOL. ML | MIXING TIME (MIN.) |
|---|---|---|---|
| DNP REMOVAL: PROGRAM 7 | | | |
| 1 | $CH_2Cl_2$ | 1 × 20 | 2 |
| 2 | DMF | 2 × 20 | 2 |
| 3 | 10% thiophenol in DMF | 1 × 20 | 25 |
| 4 | DMF | 1 × 20 | 2 |
| 5 | 10% TEA in $CH_2Cl_2$ | 1 × 20 | 5 |
| 6 | DMF | 1 × 20 | 2 |
| 7 | 10% thiophenol in DMF | 1 × 20 | 25 |
| 8 | DMF | 3 × 20 | 2 |
| 9 | methanol | 2 × 20 | 2 |
| 10 | $CH_2Cl_2$ | 3 × 20 | 2 |

| ABBREVIATIONS | |
|---|---|
| Abbreviation | Meaning |
| Ala | L-alanine |
| Arg | L-arginine |
| Asn | L-asparagine |
| Asp | L-aspartic acid |
| Cys | L-cysteine |
| Gln | L-glutamine |
| Glu | L-glutamic acid |
| Gly | glycine |
| His | L-histidine |
| Ile | L-isoleucine |
| Leu | L-leucine |
| Lys | L-lysine |
| Met | L-methionine |
| Nle | L-norleucine |
| Phe | L-phenylalanine |
| Pro | L-proline |
| Ser | L-serine |
| Thr | L-threonine |
| Trp | L-tryptophan |
| Tyr | L-tyrosine |
| Val | L-valine |
| Ac | acetyl |
| Acm | acetamidomethyl |
| Boc | tert-butyloxycarbonyl |
| Bzl | benzyl |
| 2,6-$Cl_2$—CBZ | 2,6-dichlorobenzyl |
| CBZ | benzyloxycarbonyl |
| 2-Cl—CBZ | 2-chlorobenzyloxycarbonyl |
| DNP | 2,4-dinitrophenyl |
| $NO_2$ | nitro |
| DCC | dicyclohexylcarbodiimide |
| DMF | dimethylformamide |
| HBT | 1-hydroxybenzotriazole |
| MBS | m-maleinidobenzoyl-N—hydroxysuccinimide ester |
| TFA | trifluoroacetic acid |
| TEA | triethylamine |

EXAMPLE 2

Inoculation of Animals with the Synthetic Peptide-carrier Conjugate

The peptide-carrier conjugate was inoculated into both New Zealand white rabbits and Hartley guinea pigs. Each animal received three inoculations at two week intervals. The first inoculation was supplemented with complete Freund's adjuvant and administered intradermally to the rabbits and subcutaneously to the guinea pigs. All subsequent inoculations were subcutaneous with incomplete Freund's adjuvant. Each inoculation contained 1.0 mg of the peptide-carrier conjugate in 0.5 ml of physiologic saline. Sera were prepared from the test animals immediately prior to the inoculation series and two weeks after the third injection. The sera were analyzed as described in the subsequent examples.

EXAMPLE 3

Analysis of sera for anti-peptide IgG antibodies

Each serum sample was analyzed by enzyme-linked immune adsorbent assay (ELISA). Synthetic peptide (50 mg/well) in phosphate-buffered physiologic saline (PBS) was adsorbed onto the wells of a polystyrene plate at 4° C. for 18 hours. The subsequent steps were performed at room temperature. Following peptide adsorption, each well was washed several times with PBS and 0.5% gelatin in PBS was added and allowed to adsorb for one hour. The wells were then washed once with PBS and a 1:20 dilution, in PBS, of each test serum was added in duplicate wells and allowed to react with the absorbed peptide for two hours. The wells were subsequently washed once with the 0.5% gelatin solution, twice with 0.02% Tween-20 detergent solution in PBS and three times with PBS.

A 1:250 dilution of a 1.0 mg/ml solution of goat anti-rabbit IgG or goat anti-guinea pig IgG antibodies, covalently linked to alkaline phosphatase, was then added to the appropriate wells and allowed to react for two hours. The wells were then washed twice with 0.02% Tween-20 in PBS, twice with PBS, and three times with water. Each well received 0.1% p-Nitrophenyl phosphate in 10% diethanolamine, pH 9.8, containing 0.5 mM $MgCl_2.6H_2O$. The ensuing reaction was allowed to proceed at 37° C. for 30 minutes, at which time it was terminated by the addition of sodium hydroxide.

The greater the interaction of antibodies in the test serum with the peptide substrate, the greater is the amount of alkaline phosphatase bound onto the well. The phosphatase enzyme mediates the breakdown of p-nitrophenyl phosphate into a molecular substance which absorbs visible light at a wavelength of 405 nm. Hence, there exists a direct relationship between the absorbence of 405 nm light at the end of the ELISA reaction and the amount of peptide-bound antibody.

All the rabbits and guinea pigs inoculated with the synthetic peptide-carrier conjugate developed antibodies capable of binding the peptide.

EXAMPLE 4

Analysis of Sera for Anti-hepatitis A Virion IgG Antibodies

Each serum sample was analyzed by ELISA. Mouse monoclonal antibody specific for HAV (0.5 μG) was absorbed, in PBS, onto each wells of a polystyrene plate at 4° C. for 18 hours. Following adsorption, the wells were washed twice with PBS and 400 mg/well of purified HAV in PBS added and allowed to bind to the antibody at 4° C. for 20 hours. All subsequent ELISA steps were as described in Example 3.

All the rabbits and guinea pigs inoculated with the synthetic peptide-carrier conjugate developed antibodies capable of binding to the hepatitis A virion.

EXAMPLE 5

Analysis of Sera for Antibodies which Compete with Polyspecific Antibodies from Human Anti-HAV Immune Sera The competition assay was done using the commercially available HAVAB assay kit from Abbott Labs, Chicago, Ill.

Most of the rabbits and guinea pigs inoculated with the synthetic peptide-carrier conjugate developed antibodies capable of competing antibodies from human anti-HAV immune sera.

EXAMPLE 6

Analysis of Sera for Antibodies Which Bind to the Denatured, Purified VP1 Structural Protein of HAV Reactivity of anti-peptide antibodies with the purified structural proteins of HAV was determined by an immuno-blot assay. HAV proteins were separated by electrophoresis in polyacrylamide gels Laemmli et al., Nature 277: 680–685, 1970. The separated proteins were then transferred onto nitrocellulose membranes using a Hoefer Scientific Instruments TE 42 Transphor and a transfer buffer consisting of 100 mM TRIS, pH 7.5, 16 mM glycine, 20% methanol for a 4 hour transfer at an average of 60 Volts. The nitrocellulose membrane was then blocked with 3.0% gelatin in 20 mM TRIS, pH 7.5, 500 mM NaCl (TBS). The membrane was subsequently incubated with a 1:50 dilution of the antiserum to be tested. This was followed by several TBS washes containing 0.1% Tween-20 detergent. $^{125}$I-protein A was then added to the membrane for 2.0 hours followed by several additional washes with TBS and detergent. The membrane was thoroughly dried and radioactivity associated with the HAV proteins, as a result of antibody binding, was visualized by exposure of x-ray film. All of the animals inoculated with the synthetic peptide-carrier conjugate developed antibodies which bound the denatured VPl structural protein.

EXAMPLE 7

Analysis of Sera for Activity Which Specifically Neutralizes HAV Infectivity

Newborn cynomologous monkey kidney (NBCmk) cells were set up from frozen stock cultures at a concentration of $1\times10^4$ cells/well in a 96 well plate using 0.2 ml/well of EMEM (Eagle Minimum Essential Medium) plus 10% fetal calf serum (FCS) and incubated in a $CO_2$ water-jacketed incubator at 35° C. with 5% $CO_2$ in a humidified atmosphere for 5 to 7 days until 80 to 90% confluency was attained.

The virus stock used in these assays was previously grown in the cell type to be used for the assay (i.e. NBCmK viral stock only in NBCmk cells). Although untreated HAV stock prepared by previously described procedures (U.S. Pat. No. 4,164,566) could be used in these assays, a more sensitive titer of neutralizing antibody activity can be determined with HAV treated with the detergent Na-lauryl sulfate (SLS). For this treatment, SLS from 20% stock solution was added to the stock HAV to a final concentration of 0.1%. The virus was mixed thoroughly and incubated at 37° C. for 60 minutes. The virus was dialyzed using 3 changes of phosphate buffered saline of 4 liters/change for 3 to 4 ml of HAV over a period of 36 hours. The viral solution was then removed from the dialysis bag, sterile filtered and stored in small (0.3 to 0.5 ml) aliquots at −20° C.

On the day the neutralization assay was performed, the viral stock was diluted using several 5- or 10-fold dilutions (EMEM media was used for these dilutions). Sera or tissue culture fluid containing monoclonal antibodies was added to the dilutions of HAV in either small plastic tubes or in a microtiter plate; normally 0.1 ml of each viral dilution is added and sera was added, diluted as above, from 1:4 up to 1:200 (or even higher dilutions for some hyperimmune animal sera). The mixture of virus and antisera was mixed and then incubated for 60 minutes at room temperature.

The culture media was aspirated off of the test cells and the pre-incubated virus-antibody mixture was added using separate micropipette tips for each dilution to avoid contamination. The microtiter plates of cells were rocked on a platform for 30 minutes at room temperature and then incubated in a stationary position for 3 hours at 35° C. The media was then aspirated off and fresh EMEM with 0.5% FCS, 2 mM glutamine, 50 units/ml of penicillin and 50 micrograms/ml of streptomycin was added (0.25 ml/well of a 96 well microtiter plate).

The cells were then incubated at 35° C. in a $CO_2$ water-jacketed incubator. The cells were refed on the fifth day following the infection with HAV by first removing the media by aspiration and then adding fresh EMEM with fetal calf serum, glutamine, penicillin, and streptomycin as described above.

The cells were fixed on the seventh day following infection for NBCmk cells and on the tenth to fourteenth day for LLC-MK-2 cells. For this step, the media was aspirated off and the cells were washed gently with 3 washes of 0.2 ml of PBS/wash/well. Acetone was added to fix the cells at 200 μl/well and was aspirated off very quickly so that the total contact time of acetone and cells was less than 60 seconds. The plates were air dried to remove all acetone.

$I^{125}$-labelled antibody to HAV (HAVAB, Abbott) was added to each well at 0.040 ml/well (approximately 0.15 microcuries/well). The plate was incubated for 60 minutes on a rocking platform at room temperature and then 3 hours at 35° C. in a stationary position. The $I^{125}$ antisera was then aspirated off and the wells washed 3 times with 0.3 ml of PBS/well/wash. The plates were then washed 10 times with gently running water. After air drying the plates or quickly drying in an oven, the plates were exposed to x-ray film with an intensifying screen. This exposure was done at −70° C. and lasted from 10 hours to 3 days.

Controls included (1) uninfected cells for background labelling with the $I^{125}$ antibody preparation, (2) virus dilution to which no antisera was added to determine the titer of the virus, and (3) pre- and post-inoculation sera from either mice, rats, marmosets or chimpanzees that had previously been shown to be negative and positive (respectively) for neutralizing antisera to HAV.

To determine the neutralizing titer of the sera or monoclonal antibodies, the titer of the untreated virus was first determined comparing the radioactive labelling (darkness of x-ray film) of the virus dilutions to the labelling of uninfected cells. Next, the highest antibody dilution that gave an inhibition of the growth of Hepatitis A (or less antigen made/well) was determined by comparing the wells that contained Hepatitis A plus the test sera to the viral growth with virus alone. This was done either visually or using a densitometer to scan the radioactive film to determine more accurate percentages for inhibition of growth.

Both monoclonal antibodies and sera from HAV immunized hosts were shown to have virus neutralizing activity by the foregoing assay.

All the rabbits and guinea pigs inoculated with the synthetic peptide-carrier conjugate developed HAV infectivity-neutralizing activity.

What is claimed is:

1. A peptide comprising one of the amino acid sequences:

A-Glu-Gln-Asn-Val-Pro-Asp-Pro-X, B-Glu-Ser-Arg-His-Thr-Ser-Y, or C-Asn-Ser-Asn-Asn-Lys-Glu-Tyr-Z wherein A is L-S-Thr, L-S-Ser-Thr, L-S-Val-Ser-Thr, L-S-Thr-Val-Ser-Thr, L-S-Thr-Thr-Val-Ser-Thr, or L-S-Ser-Thr-Thr-Val-Ser, and X is Gln-S-L, Gln-Val-S-L or Gln-Val-Gly-S-L, B is L-S-Gly, L-S-Pro-Gly, L-S-Lys-Pro-Gly, L-S-Leu-Lys-Pro-Gly, L-S-Glu-Leu-Lys-Pro-Gly, or Pro-Gly-Leu-Lys-Pro-Gly, and Y is Asp-S-L, Asp-His-S-L, Asp-His-Met-S-L or Asp-His-Met-Ser-S-L, C is L-S-Phe, L-S-Thr-Phe, L-S-Phe-Thr-Phe, L-S-Thr-Phe-Thr-Phe or L-S-Cys-Thr-Phe-Thr, and Z is Thr-S-L, Thr-Phe-S-L, Thr-Phe-Pro-S-L, Thr-Phe-Pro-Ile-S-L or Thr-Phe-Pro-Ile-Thr-S-L, wherein A,B,C,X,Y or Z may be present or absent, and wherein L is present or absent and is a linker amino acid selected from Lys having a free side chain or a side chain acylated with a photoreactive group, Tyr, Cys, Glu or Asp, and S is present or absent and is a spacer amino acid selected from Gly, Ala or Nle.

2. A peptide according to claim 1 having one of the following amino acid sequences:

A-Ser-Thr-Val-Ser-Thr-Glu-Gln-Asn-Val-Pro-Asp-Pro-Gln-Val-Gly-X

B-Pro-Glu-Leu-Lys-Pro-Gly-Glu-Ser-Arg-His-Thr-Ser-Asp-His-Met-Ser-Y

C-Cys-Thr-Phe-Thr-Phe-Asn-Ser-Asn-Asn-Lys-Glu-Tyr-Thr-Phe-Pro-Ile-Thr-Z wherein A, B, C, X, Y and Z are as defined in claim 1.

3. A peptide according to claim 1 having one of the following amino acid sequences:

Ac-Tyr-Nle-Ser-Thr-Glu-Gln-Asn-Val-Pro-Asp-Pro-Gln-Val-Gly-Cys-$NH_2$

Ac-Lys-Nle-Val-Ser-Thr-Glu-Gln-Asn-Val-Pro-Asp-Pro-Gln-Val-Gly-Nle-$NH_2$

Ac-Lys(BB)-Nle-Val-Ser-Thr-Glu-Gln-Asn-Val-Pro-Asp-Pro-Gln-Val-Gly-Nle-$NH_2$

Ac-Tyr-Pro-Glu-Leu-Lys-Pro-Gly-Glu-Ser-Arg-His-Thr-Ser-Asp-His-Nle-Ser-Cys-$NH_2$

Ac-Cys-Thr-Phe-Thr-Phe-Asn-Ser-Asn-Asn-Lys-Glu-Tyr-Thr-Phe-Pro-Nle-$NH_2$

Ac-Thr-Phe-Thr-Phe-Asn-Ser-Asn-Asn-Lys-Glu-Tyr-Thr-Phe-Pro-Nle-Cys-$NH_2$.

4. A peptide of claim 1 conjugated to a carrier protein.

5. A peptide of claim 2 conjugated to a carrier protein.

6. A peptide of claim 3 conjugated to a carrier protein.

7. A conjugate of claim 4 wherein the carrier protein is serum albumin, keyhole limpet hemocyanin diphtheria toxid or a synthetic polyaminoacid.

8. A conjugate of claim 5 wherein the carrier protein is serum albumin, keyhole limpet hemocyanin diphtheria toxid or a synthetic 9. A conjugate of claim 6 wherein the carrier protein is serum albumin, keyhole limpet hemocyanin diphtheria toxid or a synthetic polyaminoacid.

* * * * *